(12) United States Patent
Katura et al.

(10) Patent No.: US 7,565,192 B2
(45) Date of Patent: Jul. 21, 2009

(54) BIOLOGICAL OPTICAL MEASUREMENT SYSTEM

(75) Inventors: Takusige Katura, Tokyo (JP); Naoki Tanaka, Tokyo (JP); Hiroki Sato, Oi (JP); Akiko Obata, Hatoyama (JP); Atsushi Maki, Fuchu (JP)

(73) Assignee: Hitachi, Ltd., Tokyo (JP)

( * ) Notice: Subject to any disclaimer, the term of this patent is extended or adjusted under 35 U.S.C. 154(b) by 500 days.

(21) Appl. No.: 11/205,160

(22) Filed: Aug. 17, 2005

(65) Prior Publication Data

US 2006/0100525 A1 May 11, 2006

(30) Foreign Application Priority Data

Oct. 21, 2004 (JP) .............................. 2004-306319

(51) Int. Cl.
*A61B 5/00* (2006.01)
(52) U.S. Cl. ...................................... 600/476; 600/479
(58) Field of Classification Search ................. 600/544, 600/473, 529, 427, 407, 509–514, 554, 545, 600/378, 476, 479, 301
See application file for complete search history.

(56) References Cited

U.S. PATENT DOCUMENTS

| | | | | | |
|---|---|---|---|---|---|
| 4,201,224 | A | * | 5/1980 | John | 600/544 |
| 4,315,319 | A | * | 2/1982 | White | 702/104 |
| 5,020,538 | A | * | 6/1991 | Morgan et al. | 600/409 |
| 5,253,646 | A | | 10/1993 | Delpy et al. | |
| 5,655,534 | A | * | 8/1997 | Ilmoniemi | 600/408 |
| 5,857,978 | A | * | 1/1999 | Hively et al. | 600/544 |
| 6,731,975 | B1 | * | 5/2004 | Viertio-Oja et al. | 600/544 |
| 6,805,673 | B2 | * | 10/2004 | Dekker | 600/529 |
| 6,987,994 | B1 | * | 1/2006 | Mortz | 600/336 |

2001/0018554 A1 8/2001 Yamashita et al.

(Continued)

FOREIGN PATENT DOCUMENTS

EP 290273 A1 11/1988

(Continued)

OTHER PUBLICATIONS

D. Boas, et al., "Diffuse Optical Imaging of Brain Activation: Approaches to Optimizing Image Sensitivity, Resolution, and Accuracy", NeuroImage, Sep. 11, 2004, pp. 275-288.

(Continued)

*Primary Examiner*—Eric F Winakur
*Assistant Examiner*—Lawrence N Laryea
(74) *Attorney, Agent, or Firm*—Mattingly & Malur, P.C.

(57) ABSTRACT

A typical task assigned for measuring a brain activity signal lasts from 10 to 30 seconds. The frequency band of the Mayer wave noise signal is very close to the frequency bands of brain activity signals, a result, it is difficult to reduce the Mayer wave noise signal using a bandpass filter or a bandcut filter. Light irradiating units and light detecting units for detecting the emitted light that has been passed through or reflected within the tissue are provided. A biological signal measuring unit measures at least one of the pulsation, breathing, blood pressure, and temperature. The relationship between an optical signal obtained by the light detecting unit and a biological signal using non-linear analysis; and a computation for separating the biological noise signal from the optical signal on the basis of the obtained relationship.

5 Claims, 9 Drawing Sheets

U.S. PATENT DOCUMENTS

| | | | |
|---|---|---|---|
| 2001/0047131 A1 | 11/2001 | Maki et al. | |
| 2002/0028997 A1* | 3/2002 | Ito et al. | 600/476 |
| 2002/0141624 A1 | 10/2002 | Gil et al. | |
| 2004/0106856 A1 | 6/2004 | Kimura | |

FOREIGN PATENT DOCUMENTS

| | | |
|---|---|---|
| EP | 1428471 A2 | 6/2004 |
| EP | 1452136 A | 9/2004 |
| JP | 07-308295 | 11/1995 |
| JP | 2002-172094 | 6/2002 |
| WO | 03/071938 A | 9/2003 |

OTHER PUBLICATIONS

U. Feldmann et al., "Predictability Improvement as an Asymmetrical Measure of Interdependence in Bivariate Time Series", International Journal of Bifurcation and Chaos, vol. 14, No. 2, 2004, pp. 505-514.

"Noninvasive measurement of neuronal activity with near-infrared optical imaging" by Franceshini, et al. pp. 372-386.

Tanaka et al, "Statistical test for general causality and its application to physiological date", Proceedings of the 2004 IEICE Engineering Sciences Society Conference Sep. 8, 2004, p. 54. & English translation.

* cited by examiner

FIG.9

BIOLOGICAL OPTICAL MEASUREMENT SYSTEM

CLAIM OF PRIORITY

The present application claims priority from Japanese application JP 2004-306319 filed on Oct. 21, 2004, the content of which is hereby incorporated by reference into this application.

BACKGROUND OF THE INVENTION

1. Field of the Invention

The present invention relates to an optical measurement technology and particularly to an optical measurement method and apparatus for acquiring biological information based on optical signals received from a tissue.

2. Background Art

Measurement signals (to be hereafter referred to as an optical signal) obtained by optically acquiring internal information about a living tissue (such as in JP Patent Publication (JP Patent Publication (Kokai) No. 9-135825 A (1997)) contain noise signals due to several factors, in addition to the target response signal. To reduce the influence of such noise signals, averaging or other techniques using a bandpass filter, for example, are used.

The averaging method for reducing noise signal is based on the premise that the brain activities show uniform responses to the same tasks, for example. The method employing a bandpass filter for reducing noise signal is based on the premise that a response signal and a noise signal exist in different frequency bands. These are processes for dealing with multiple noise signals. Processes attuned to noise signals due to specific causes have also been considered.

For example, in the case of a noise signal due to the influence of pulsation (pulsation noise signal), the frequency can be easily identified, so that the noise signal can be reduced using a bandcut filter. In another example, the pulsation noise signal contained in an optically measured signal is reduced on the basis of a pulsation signal measured at a certain location, such as at the ear (Patent Document 2). In yet another example, a pulsation noise signal is extracted from the optically measured signal and its influence is reduced (Non-patent Document 1). However, the actual brain activities do not necessarily produce uniform responses to the same tasks, and the signal processing scheme using averaging does not always produce successful results.

Even if the signal processing based on averaging is effective, it takes much time for acquiring signals to be summed. Further, some noise signals in the optical signal contain irregular components with a frequency band of approximately 0.1 Hz. These components are a kind of fluctuation signal that is inherently possessed by living bodies and are referred to as a low-frequency fluctuation signal or the Mayer wave.

Regarding the Mayer wave, a number of studies have so far been conducted, and the involvement of fluctuations in blood pressure and heart beat or heart rate has been indicated. However, not much light has been shed on the details of its occurrence mechanism. In this connection, it is noted that in the case of Patent Document 1, noise is eliminated by subtraction using a pulsation signal, and therefore the Mayer wave noise component, which cannot be readily obtained from the pulsation signal, cannot be eliminated by subtraction of the pulsation signal.

Patent Document 1: JP Patent Publication (Kokai) No. 9-135825 A (1997)

Patent Document 2: JP Patent Publication (Kokai) No. 2004-173751 A

Patent Document 3: JP Patent Publication (Kokai) No. 7-308295 A (1995)

Patent Document 4: JP Patent Publication (Kokai) No. 2002-172094 A

Non-patent Document 1: Maria Angela Franceschini et al., NeuroImage 21 (2004) 372-386

SUMMARY OF THE INVENTION

Generally, the task assigned for measuring brain activity signals lasts for 10 to 30 seconds. This is the time required for inducing a sufficient amount of brain activity such that a measurable state of brain activity can be obtained. The frequency bands of the brain activity signals that can be acquired by the task lie between approximately 0.03 and 0.1 Hz. Therefore, because the frequency band of the Mayer wave noise signal is very close to the frequency bands of brain activity signals, it is difficult to reduce the Mayer wave noise signal using bandpass filters or bandcut filters.

In addition, because the low-frequency fluctuation signal contains irregular and non-periodic changes, it is difficult to reduce them using a simple frequency filter.

Thus, in order to solve these problems of the prior art, attempts must be made to reduce biological noise signals based on an analysis of the influence of biological signals, such as blood pressure and heart beat or heart rate, on an optical signal.

To measure the blood dynamics inside the tissue of a test subject, the invention provides a system comprising one or more light irradiating units for irradiating the subject with light; one or more light detecting units for detecting the emitted light that has been passed through or reflected within the tissue; a biological signal measuring unit for measuring one or a combination of two or more factors selected from pulsation, breathing, blood pressure, and body temperature; means for analyzing the relationship between an optical signal obtained by the light detecting unit and a biological signal using non-linear analysis; and means for performing a computation for separating biological noise signal from the optical signal using the obtained relationship.

This is based on the fact that the influence of biological signals such as blood pressure and heart beat or heart rate on an optical signal consists of a complex combination of individual factors, and that they have a non-linear relationship rather than a linear relationship. Therefore, by computing the relationship between the biological signals and the optical signal by non-linear analysis, the biological noise signal can be determined and separated from the optical signal.

By "optical measurement" herein is meant the measurement of changes in hemoglobin concentration in the tissue by the aforementioned one or more light irradiating units for irradiating a subject with light, and one or more light detecting units for detecting the emitted light that has been passed through or reflected within the tissue. The term "optical signal" herein refers to a signal obtained by such an optical measurement.

By "the measurement of a biological signal" herein is meant the measurement performed by the aforementioned biological signal measurement unit for measuring one or a combination of two or more factors selected from pulsation, breathing, blood pressure, and body temperature. The term "biological signal" herein refers to a signal obtained by such a measurement.

In accordance with the invention, an optical signal and biological signals including one or more factors measured in synchronism with the optical measurement are obtained. The relationship between the optical signal $S_{OT}$ and the biological signal $S_{BS}$ is then subjected to non-linear analysis so as to obtain the following equation regarding a biological noise signal $S_{BN}$:

$$S_{BN} = f(S_{BS}) \quad (1)$$

where $S_{BN}$ and $S_{BS}$ are each one or more signals. Function f may be either linear or non-linear. The thus calculated biological noise signal $S_{BN}$ is then subtracted from the optical signal $S_{OT}$ according to the following equation (2), thereby obtaining an optical signal $S_P$ in which the influence of the biological noise signal has been reduced:

$$S_P = S_{OT} - S_{BN} \quad (2)$$

In accordance with the invention, the amount of biological noise signal contained in a biological optical measurement signal can be reduced.

DESCRIPTION OF PREFERRED EMBODIMENTS OF THE INVENTION

Embodiment 1

Figure 1:
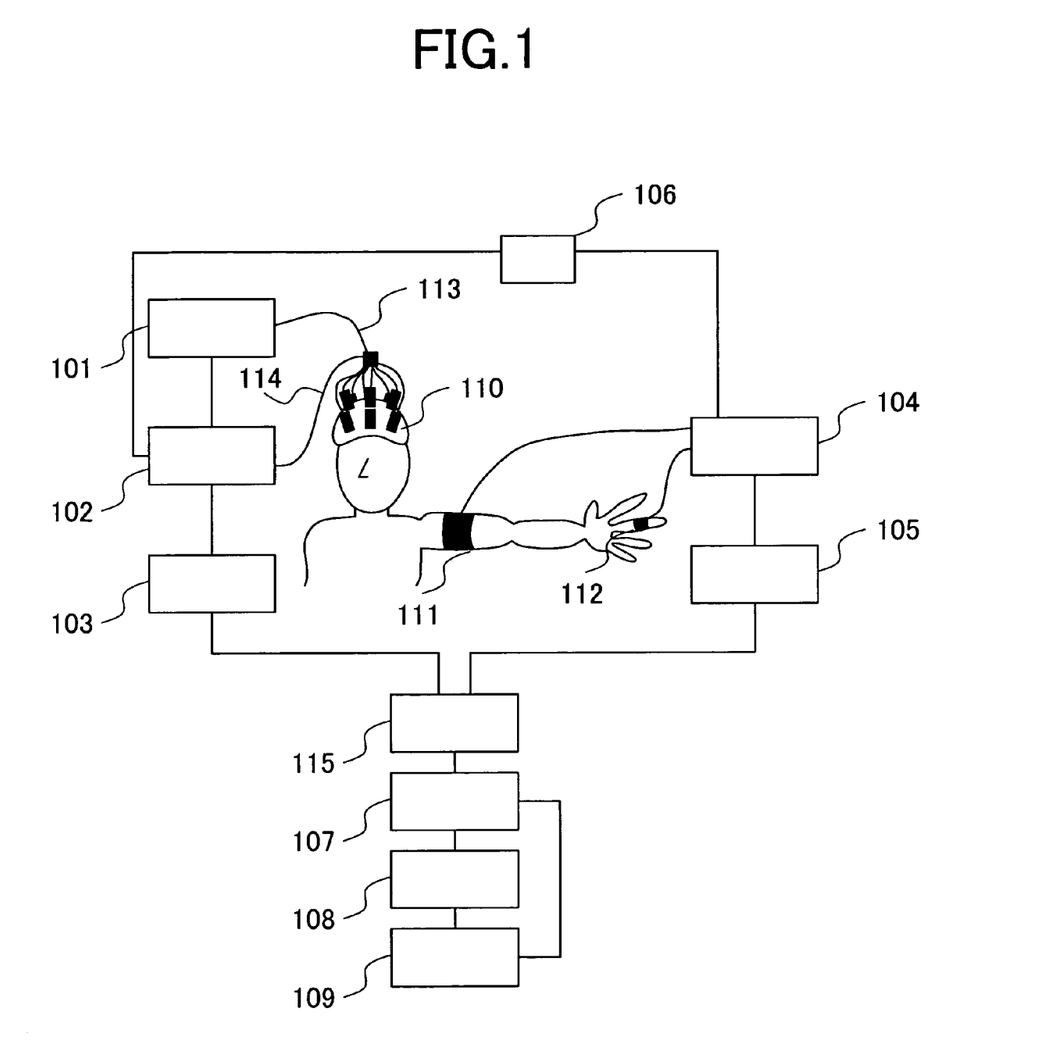
FIG. 1 shows a diagram of a system according to a first embodiment of the invention.

FIG. 1 shows a diagram of a system according to a first embodiment of the invention.

In the first step of a procedure, the operator attaches a biological optical measuring probe 110 to a part or the entirety of the head of a subject. The tissue is then irradiated with light produced by a light irradiating unit 101 via optical fibers 113 connected to the biological optical measuring probe 110. The light that has passed through the tissue is then detected by an optical detection unit 102 via an optical fiber 114 connected to the biological optical measuring probe 110. The resultant signal is recorded in a memory unit 103.

The aforementioned signal recorded in the memory unit 103 is hereafter referred to as "an optical signal." A blood-pressure measuring cuff 111 for the arm and a blood-pressure measuring cuff 112 for the finger are attached to the arm and a finger, respectively, of the subject. The cuffs, either one of which may be dispensed with, are controlled by a heatbeat/blood pressure measuring apparatus 104, and the resultant signals are recorded in the memory unit 105.

Figure 2:
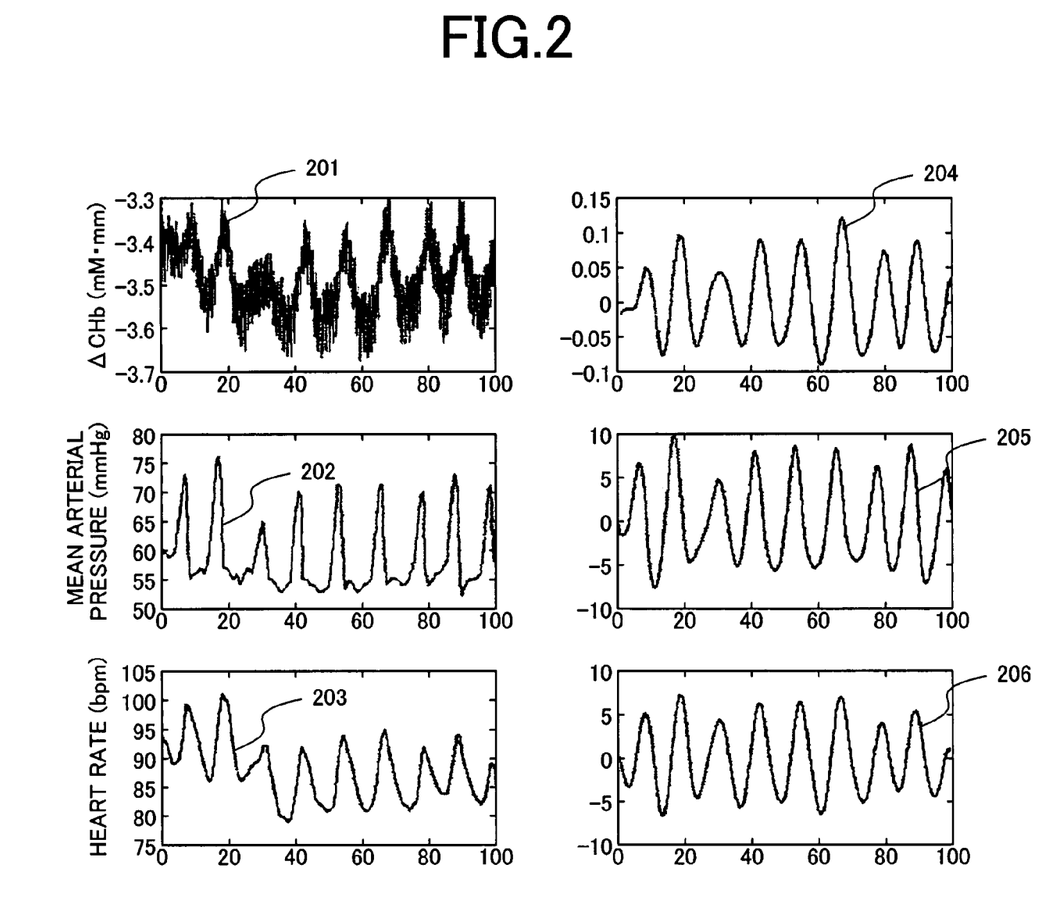
FIG. 2 shows an example of the display of a measurement signal and the measurement signal that has been passed through a bandpass filter. The horizontal axis shows the time (seconds) and the vertical axis shows the signal intensity.

The aforementioned signals recorded in the memory unit 103 are hereafter referred to as "a heart beat or heart rate signal" and "a blood pressure signal." The timing of measurement can be synchronized between the units 102 and 104 by a synchronizing unit 106. The resultant optical signal and biological signals are analyzed in a relationship computing unit 107. Specifically, the low-frequency components (which are the signal components in frequency bands lower than the frequency of heart beat or heart rate) of the both signals are extracted using a bandpass filter. For example, FIG. 2 shows an optical signal 201, a blood pressure signal 202, a heart beat or heart rate signal 203, an extracted low-frequency component of optical signal 204, an extracted low-frequency component of a blood pressure signal 205, and an extracted low-frequency component of a pulsation signal 201. The horizontal axis shows time (seconds), and the vertical axis shows signal intensity.

Figure 3:
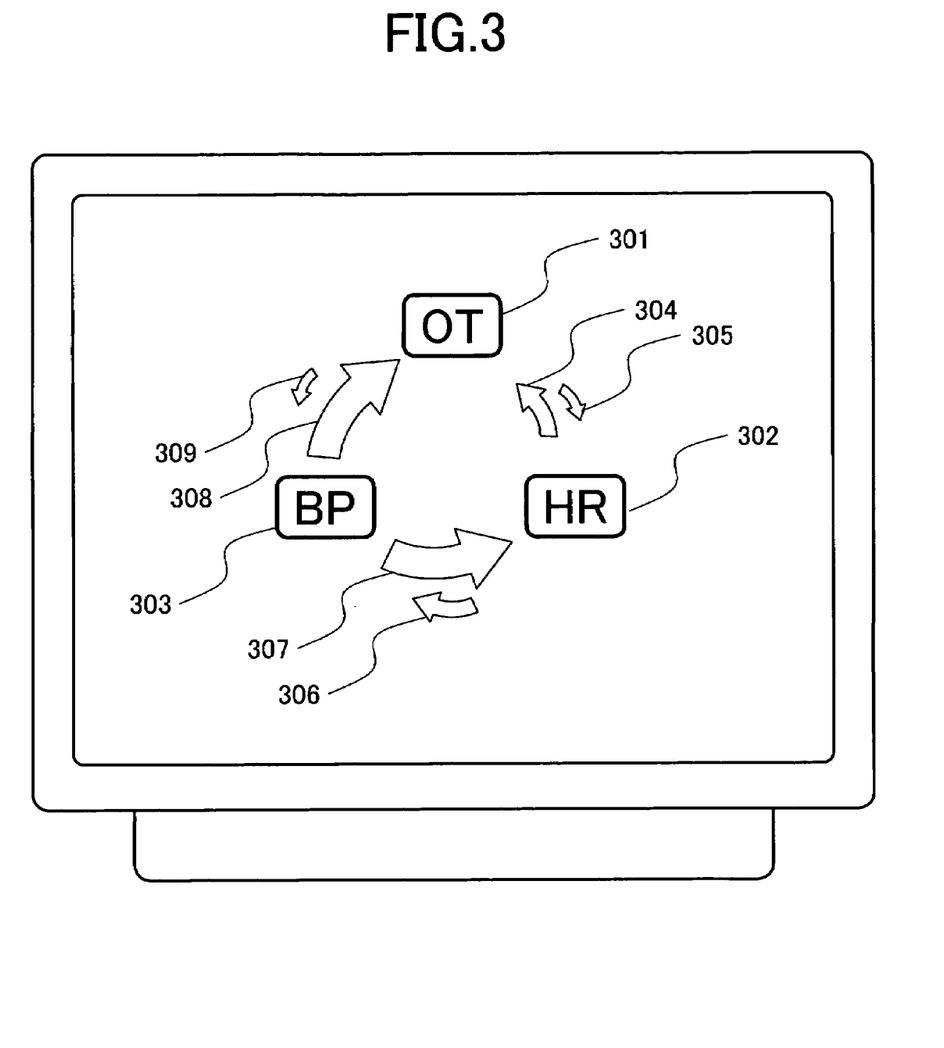
FIG. 3 shows an example of display of the extent of transfer of information among individual factors determined from the result of calculation of transfer entropy.

The relationship among the signals 204, 205, and 206 is then analyzed by the relationship computing unit 107. The relationships among the signals 204, 205, and 206 are multiple tissue indices that are related to one another in a complex manner and are not simply linear. Therefore, they call for a relationship analyzing method that is not influenced by whether a given relationship is linear or not. Accordingly, an analysis based on transfer entropy (which will be described in detail later), which is one of non-linear analysis methods is used. The indices obtained by this method are such that the relationship of any target system, be it linear or non-linear, can be analyzed. FIG. 3 shows an example of display of the extent of transfer of information among individual factors determined from the result of computation of transfer entropy.

This example is displayed on display unit 109. FIG. 3 shows the extent of flow of information among the optical signal, blood pressure signal, and heart beat or heart rate signal by the direction of each arrow and its magnitude, as well as an optical signal mark 301, a blood pressure signal mark 303, and a heart beat or heart rate signal mark 302. Specifically, the extent of transfer of information from heart beat or heart rate signal to optical signal is indicated by arrow 304; the extent of transfer of information from optical signal to heart beat or heart rate signal by arrow 305; the extent of transfer of information from heart beat or heart rate signal to blood pressure signal by arrow 306; the extent of transfer of information from blood pressure signal to heart beat or heart rate signal by arrow 307; the extent of transfer of information from blood pressure signal to optical signal by arrow 308; and the extent of transfer of information from optical signal to blood pressure signal by arrow 309. The display may involve average values within a certain period of time, or it may show the changes at each time continuously. Using an obtained value TE of entropy, a biological noise signal $S_{BN}(t)$ is calculated in a separation computing unit 108 according to the following equations (3) and (4):

$$S_{BN}(t) = f(S_{HR}(t), S_{BP}(t)) = a_0 + a_1 g(S_{HR}(t)) + a_2 g(S_{BP}(t)) \quad (3)$$

$$g(S(t)) = \sum_{\tau=\tau_1}^{\tau_2} \exp(TE(\tau)) S(t+\tau) \quad (4)$$

Although the above function f is a linear combination of function g, it may alternatively be determined from function f using a neural network. The coefficients $\alpha_0$, $\alpha_1$, and $\alpha_2$ are determined by the least squares method. Besides equation (4), the g function may be selected from other appropriate functions, such as:

$$g(S(t)) = \sum_{\tau=\tau_1}^{\tau_2} \log(TE(\tau))S(t+\tau) \quad (5)$$

and $$g(S(t)) = \sum_{\tau=\tau_1}^{\tau_2} TE(\tau)^\alpha S(t+\tau) \quad (6)$$

Figure 4:
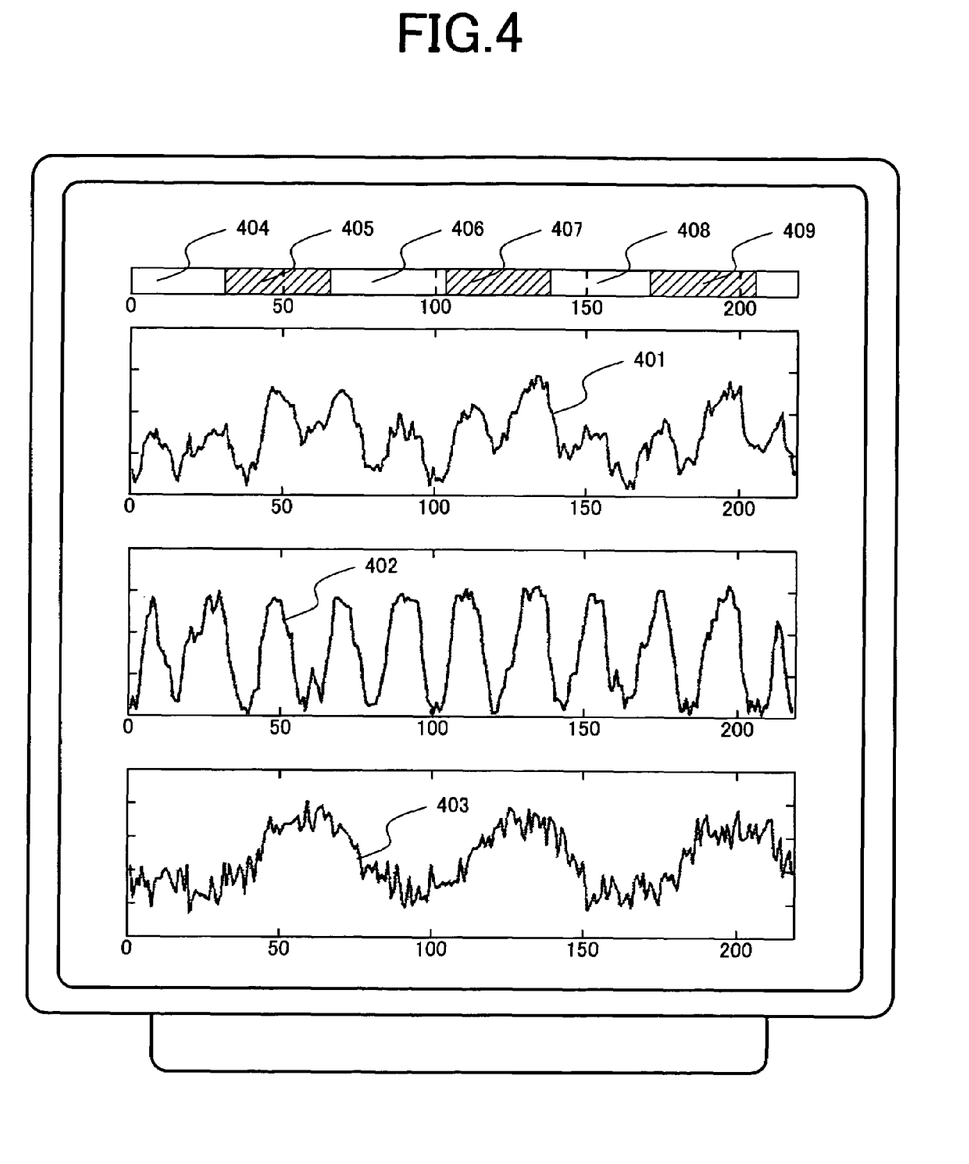
FIG. 4 shows an optical signal, a predicted biological noise signal, and a signal in which the influence of low-frequency fluctuation noise has been reduced. The horizontal axis shows time (seconds), and the vertical axis shows signal intensity.

If equation (6) is used, $\alpha$ may be determined in advance by the least squares method, for example. FIG. 4 shows an example 402 of a biological noise signal predicted from an example 401 of optical signal based on a first rest period 404, a first task period 405, a second rest period 406, a second task period 407, a third rest period 408, and a third task period 409. The horizontal axis shows the time (seconds), and the vertical axis shows the signal intensity. In example 401, although there should be obtained response signals corresponding to three periods because the example involves three repetitions of a combination of the rest periods and task periods, no such response signals are obtained due to the influence of noise. The thus predicted biological noise signal 402 is then subtracted from the optical signal 401, thereby obtaining an example 403 of a signal in which the influence of the low-frequency fluctuation is reduced.

It can be seen from the drawing that the response signal 403 is clearer than the response signal 401, which was rather obscure. These charts are shown on the screen so that the operator can monitor them. The computation of transfer entropy is performed based on any or all of the signals concerning the first rest period 404, second rest period 406, and third rest period 408. The computation of the biological noise signal $S_{BN}$ during the first task period 405, second task period 407, and third task period 409 is performed using the function f based on the transfer entropy computed during the rest periods. If the rest period is provided before each task period, function f based on the transfer entropy computed using the signal from the rest period immediately before the task period may be used for the computation of the biological noise signal $S_{BN}$ during the task period.

In addition to the combination of the heart beat or heart rate and the blood pressure, other biological signals, such as signals concerning the breathing, body temperature, and the movement of the throat, may be used in combination. For the measurement of the heart beat or heart rate, the optical irradiation and detection mechanism of optical topography equipment may be used. The heart beat or heart rate component contained in an optical topography measurement signal may be extracted and used as the heart beat or heart rate signal. Instead of the measurement of blood pressure, a heart beat or heart rate signal transmission time may be determined from heart beat or heart rate measurement signals obtained at a plurality of sites, and then a blood pressure signal may be calculated by the method disclosed in Patent Document 3.

It is important to eliminate low-frequency fluctuation signals that cannot be eliminated by the conventional simple filtering technology, for the measurement of brain activity signals at low frequency bands. In view of this fact, the biological noise signals during the measurement of brain functions can be effectively reduced by separating, particularly, biological noise signals (such as blood pressure) with fluctuations at bands lower than those of the frequency of the heart beat or heart rate.

Embodiment 2

Figure 5:
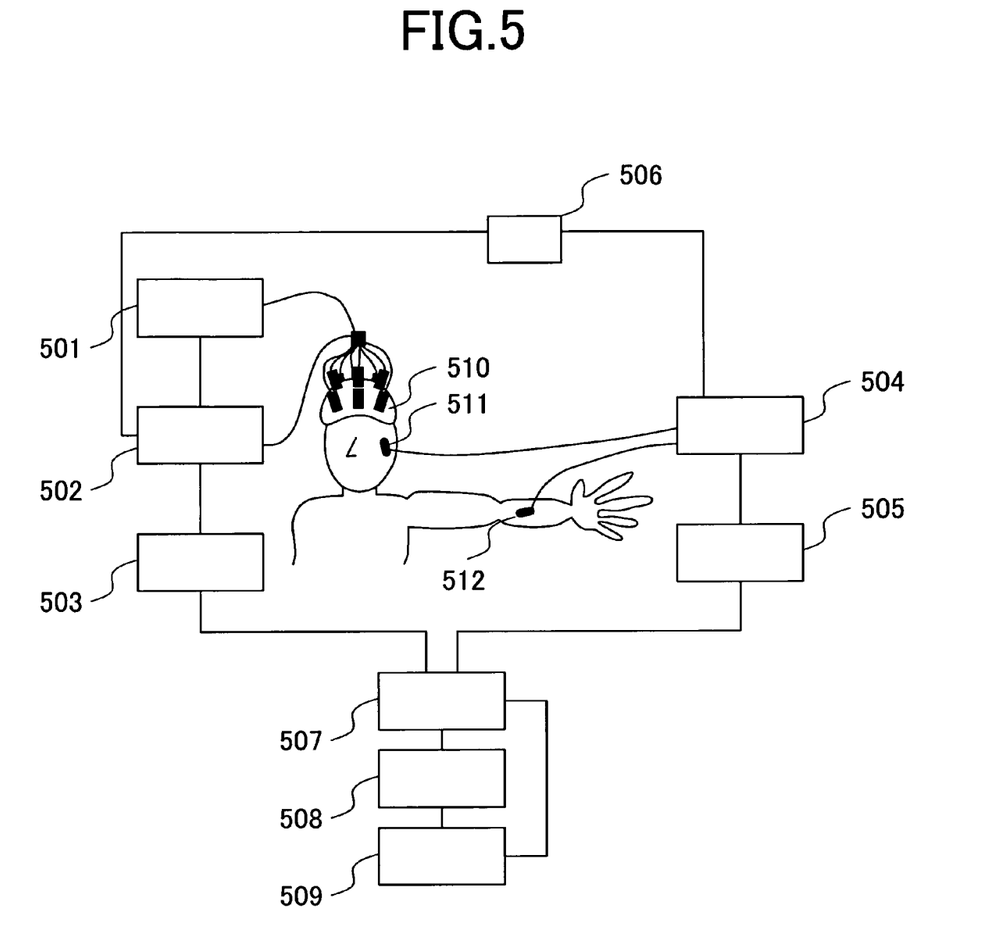
FIG. 5 shows a diagram of a system according to a second embodiment of the invention.

FIG. 5 shows a second embodiment of the invention, in which, instead of the blood pressure measuring cuff 111 for the arm and the blood pressure measuring cuff 112 for the finger in the first embodiment, probes 511 and 512 for the measurement of pulsation using light are employed. The device for measuring pulsation using light is known as a pulse oximeter, the measurement principle of which is the same as that of the present embodiment. The probes for pulsation measurement using light consist of one (511) that is disposed near the head, where optical measurement takes place, such as at the ear or the forehead, and/or the other (512) that is attached to a portion of the subject that is spaced apart from the probe 511 by a certain distance, such as the arm. Signals obtained by the pulsation measurement unit 504 are processed by units including the memory unit 505 and the relationship computing unit 507, as in the first embodiment.

Embodiment 3

Figure 6:
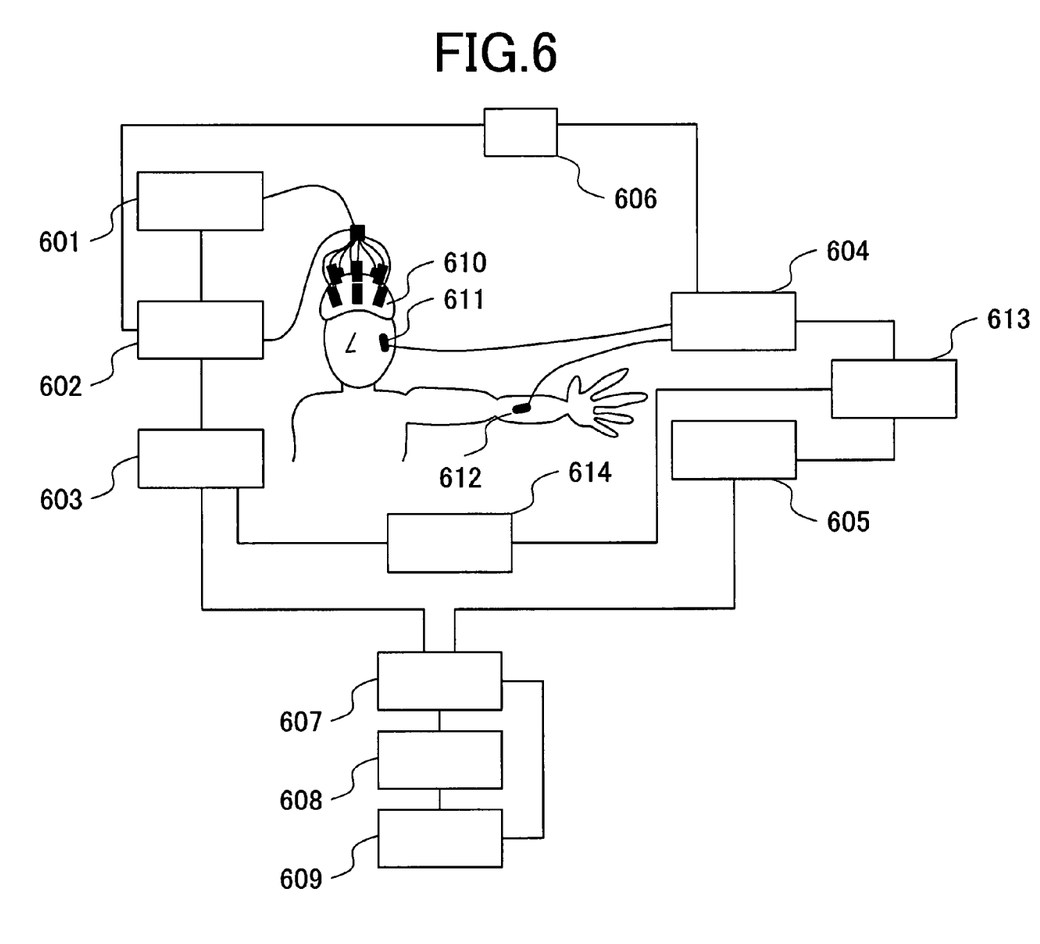
FIG. 6 shows a diagram of a system according to a third embodiment of the invention.

FIG. 6 shows a third embodiment of the invention, which includes a measurement unit that is identical to the one in Embodiment 5. A blood-pressure computing unit 613 determines the blood pressure from two signals obtained by a pulsation measurement unit 604 based on the pulsation transfer time (Patent Document 4). Alternatively, the pulsation component may be extracted from an optical signal obtained by an optical detection unit 602 and then used in the blood pressure computation unit 613.

Embodiment 4

Figure 7:
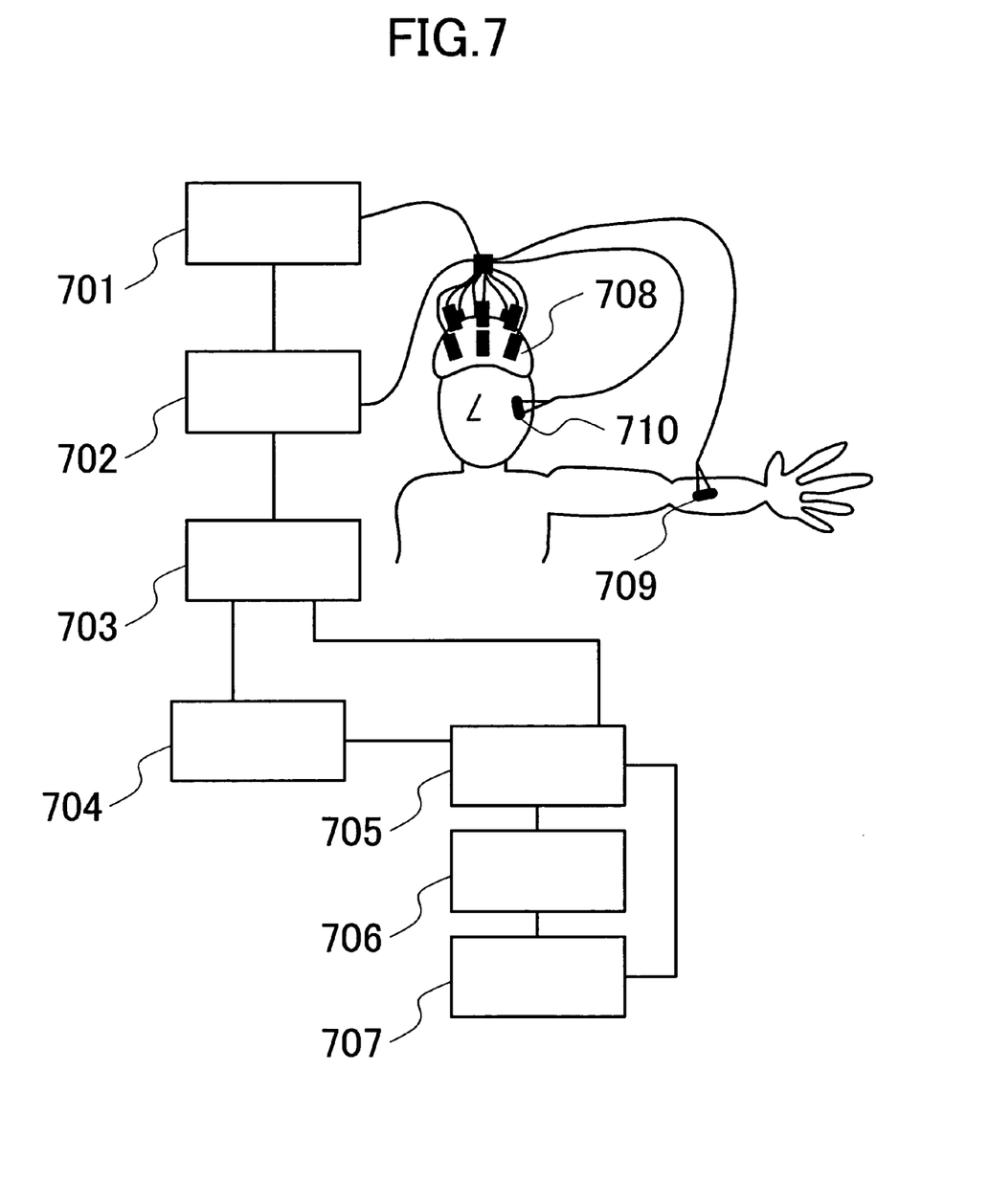
FIG. 7 shows a diagram of a system according to a fourth embodiment of the invention.

FIG. 7 shows a fourth embodiment of the invention, in which the pulsation measurement unit 504 and the memory unit 505 of the second embodiment are commonly realized with a light irradiating unit 701 for optical measurement, a light detecting unit 702, and a memory unit 703. A fluctuation signal is extracted from an obtained signal by a fluctuation extraction unit 704. In addition to the signals from fluctuation measurement probes 709 and 710, a fluctuation signal may also be extracted in the fluctuation extraction unit 704 from an optical signal produced by a biological optical measuring probe 708 for optical measurement and then used for subsequent computations.

Embodiment 5

Figure 8:
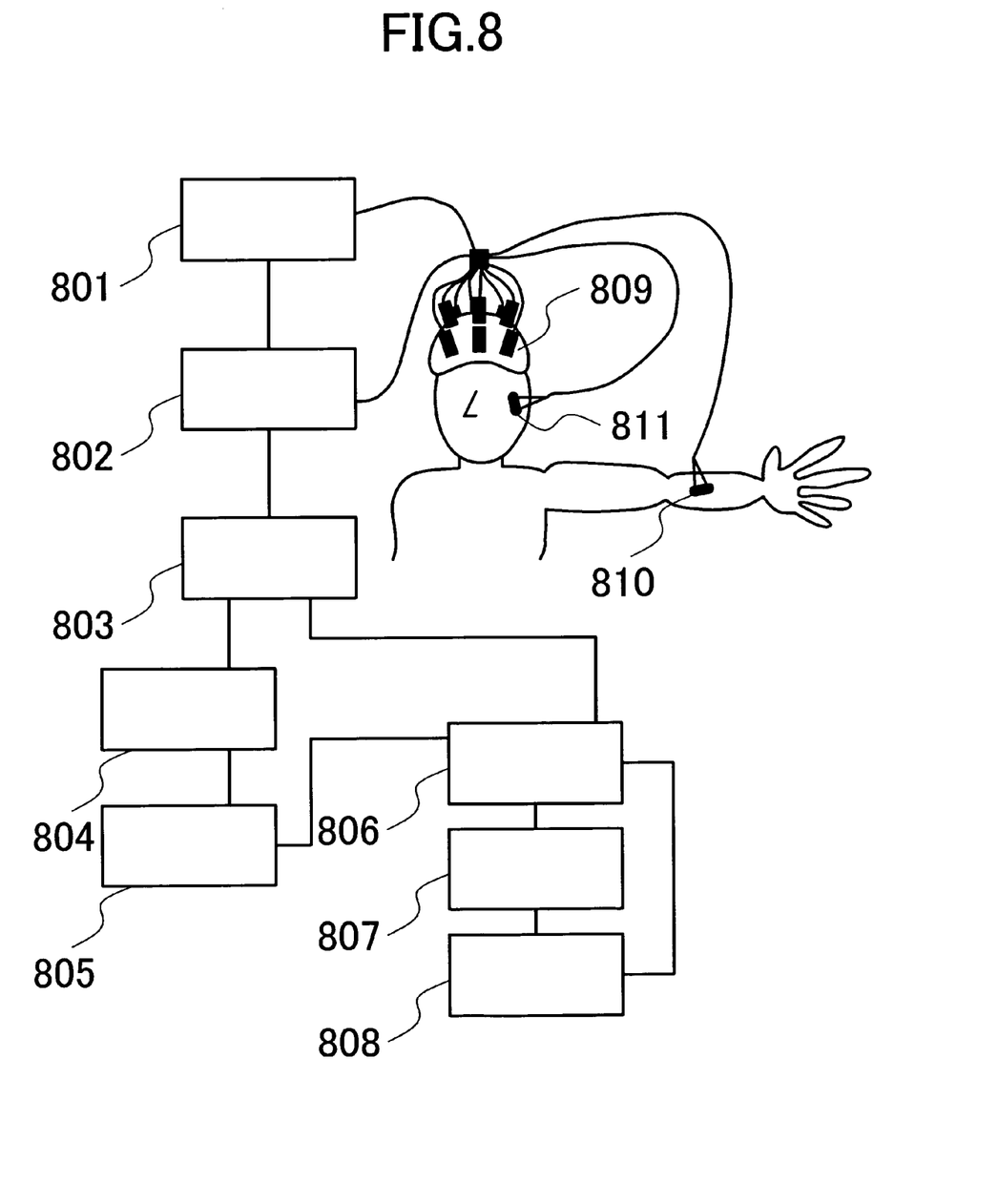
FIG. 8 shows a diagram of a system according to a fifth embodiment of the invention.

FIG. 8 shows a fifth embodiment of the invention, which is a variation of the fourth embodiment in which a blood pressure computation unit 805 is further added.

Embodiment 6

Figure 9:
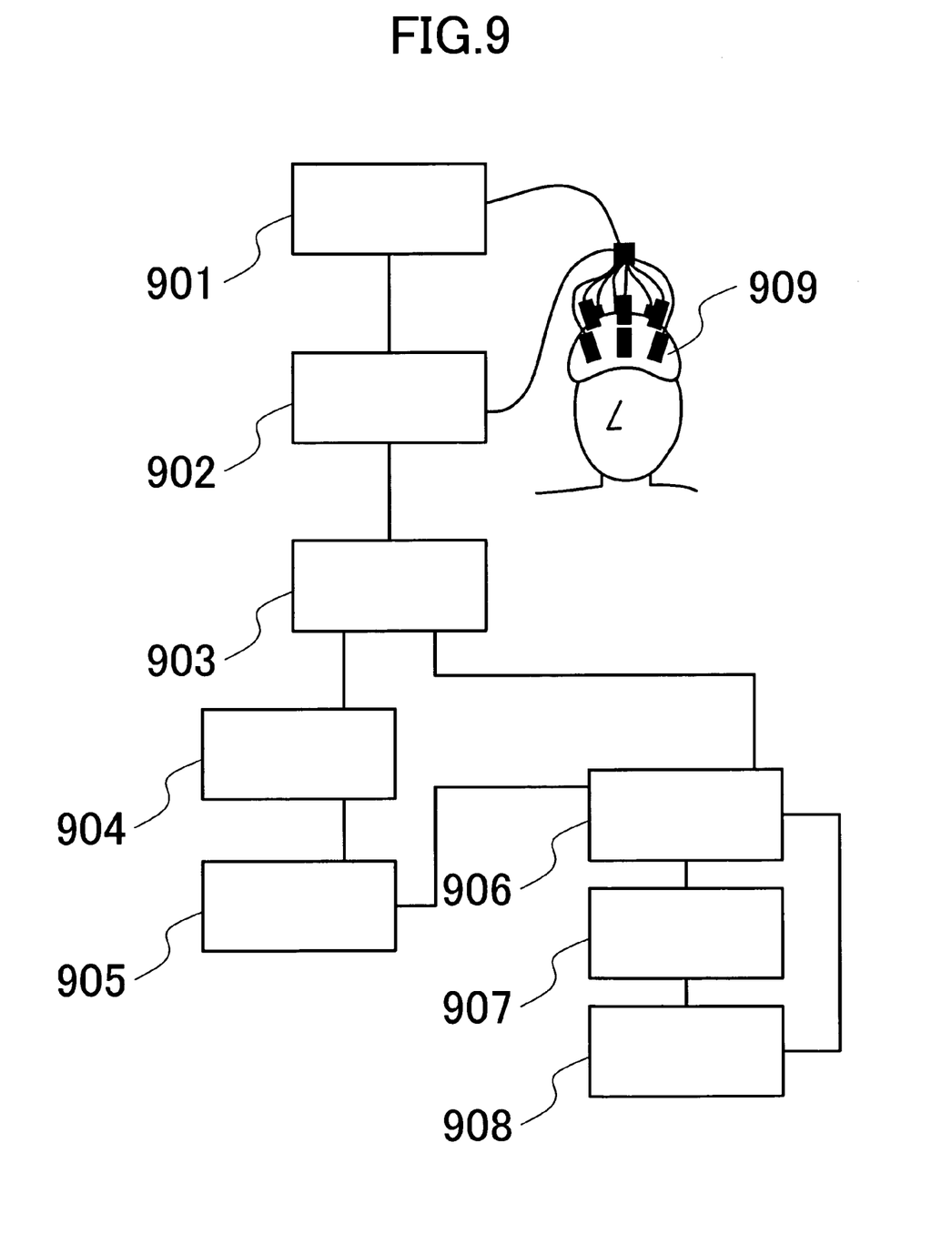
FIG. 9 shows a diagram of a system according to a sixth embodiment of the invention.

FIG. 9 shows a sixth embodiment of the invention, which is a variation of the fifth embodiment from which the fluctuation measurement probes 709 and 710 have been removed.

Regarding "Transfer Entropy"

A time-series signal measured for a certain factor possesses a certain amount of information (as defined by Shannon).

When a plurality of factors are considered, if there is some relationship between the factors, the index showing to what extent the amount of information of one is related to those of other factors is referred to as transfer entropy. Transfer entropy is fundamentally an index that is obtained for the relationship between two factors. Therefore, when analyzing multiple factors, transfer entropy is calculated for each of the combinations of two of the factors, and then the direction and extent of transfer can be identified from the magnitude of the transfer entropies. For example, when three factors A, B, and C are considered, there are six combinations, namely, A→B, B→A, B→C, C→B, C→A, and A→C. Transfer entropy is calculated for each of the combinations, and, based on their relationship in terms of magnitude, it can be clarified how information is being transferred among the factors. In accordance with the invention, the biological signal that has the greatest influence on an optical topography signal is determined based on the thus calculated transfer entropies, such that biological noise signals can be separated from the optical topography signal using such a biological signal.

Transfer Entropy Among Three or More Factors

In the case of transfer of information among three or more factors, because there are interruptions among the factors, the net transfer entropy in each combination cannot be accurately determined. Therefore, the transfer of information that exists solely in a combination of interest and that does not exist in other combinations is focused, and the net transfer entropy (intrinsic transfer entropy) is determined by the following method.

$$TE(X, Y, (Z), \tau) = \left\langle \log_2 \frac{p_{Y|YZX}(y(t+\tau) | y(t), z(t), x(t))}{p_{Y|YZ}(y(t+\tau) | y(t), z(t))} \right\rangle,$$

$$= \left\langle \log_2 \frac{p_{YYZX}(y(t+\tau), y(t), z(t), x(t))p_{YZ}(y(t), z(t))}{p_{YYZ}(y(t+\tau), y(t), z(t))p_{YZX}(y(t), z(t), x(t))} \right\rangle,$$

where $p_{YYX}(y(t+\tau)|y(t), x(t))$ is the probability of variable Y taking $y(t+\tau)$ at time $t+\tau$ when variables X and Y take $x(t)$ and $y(t)$. $p_X(x(t))$, $p_Y(y(t+\tau))$ is the probability density of variables X and Y taking $x(t)$ and $y(t+\tau)$, and $p_{XY}(x(t), y(t+\tau))$ is the probability density of their coupling.

The question is how to estimate such various probability density functions. In a method for estimating the probability density function p, the following simplified kernel expression is used with respect to a time series with length N:

$$\hat{p}^r_{YYX}(y(t+\tau), y(t), x(t)) = \qquad (9)$$

$$\frac{1}{N-\tau} \sum_{t'=1}^{N-\tau} \Theta \left( r - \left\| \begin{array}{c} y(t'+\tau) - y(t+\tau) \\ y(t') - y(t) \\ x(t') - x(t) \end{array} \right\|_{max} \right)$$

where Θ is a step function defined by:

$$\Theta(z) = \begin{cases} 1 \text{ for } z \geq 0 \\ 0 \text{ for } z < 0 \end{cases}$$

$\|\cdot\|_{max}$ indicates the maximum value distance, and r is the numerical accuracy of this probability density estimation. With regard to r, an optimum value must be defined depending on the data of concern. Generally, when there exist Z1, Z2, . . . , and Zn, by re-defining the Z in equation (1) as a vector quantity such that Z=(Z1, Z2, . . . , Zn), we have a general intrinsic transfer entropy equation for n+2 factors. This method may be used for the actual calculation of transfer entropy.

By applying the invention to the measurement of brain functions using light in the field of medicine and other researches, the influence of biological noise signal can be reduced and the S/N of the target signal can be improved, so that measurement time can be reduced and the quality of data can be improved.

What is claimed is:

1. A living body optical measurement system for measuring changes in the dynamics of blood in the brain of a test subject, said system comprising:
    light-irradiating means for irradiating the head of a test subject with light;
    light-receiving means for receiving the light emitted by said light-irradiating means that has propagated through the head of said test subject and obtaining an optical signal;
    living-body signal detecting means for detecting a living-body signal from said test subject;
    living-body noise signal computation means for computing $S_{BN}(t)$ from a product of a transfer entropy TE(τ) and S(t +τ), where S(t) and $S_{BN}(t)$ represent a living-body signal and a living-body noise signal, respectively, at time t; and
    separation computation means for separating said living-body noise signal from said optical signal.

2. The living-body optical measurement system according to claim 1, wherein said time t represents time $\tau_1$ and $\tau_2$ which differ from each other, and wherein said living-body noise signal computation means computes said living-body noise signal from a sum of the product of said transfer entropy and said living-body signal at the time $\tau_1$ and the product of said transfer entropy and said living-body signal at the time $\tau_2$.

3. The living-body optical measurement system according to claim 1, wherein said living-body signal detecting means detects a plurality of living-body signals of said test subject, and wherein said living-body noise signal computation means computes a product of each of said living-body signals and a transfer entropy between said optical signal and each of said living-body signals, thereby determining living-body noise signals of the respective living-body signals, and adds up the living-body noise signals to determine a living-body noise signal of said test subject.

4. The living-body optical measurement system according to claim 3, wherein said living-body signals are a heartbeat signal and a blood pressure signal.

5. The living-body optical measurement system according to claim 1, wherein said separation computation means subtracts said living-body noise signal from said optical signal.

* * * * *